(12) United States Patent (10) Patent No.: US 9,346,053 B2
Samuhel et al. (45) Date of Patent: May 24, 2016

(54) METHOD AND APPARATUS FOR FLUID DISPENSATION, PREPARATION AND DILUTION

(75) Inventors: Frank Samuhel, Dromana (AU); Adam Donath, Richmond (AU); Krzysztof Zawadzki, Knoxfield (AU); Anthony Cecil White, Ascot Vale (AU)

(73) Assignee: LEICA BIOSYSTEMS MELBOURNE PTY LTD, Victoria (AU)

( * ) Notice: Subject to any disclaimer, the term of this patent is extended or adjusted under 35 U.S.C. 154(b) by 1286 days.

(21) Appl. No.: 10/551,642

(22) PCT Filed: Mar. 31, 2004

(86) PCT No.: PCT/AU2004/000407
§ 371 (c)(1),
(2), (4) Date: Apr. 2, 2010

(87) PCT Pub. No.: WO2004/088327
PCT Pub. Date: Oct. 14, 2004

(65) Prior Publication Data
US 2010/0191382 A1 Jul. 29, 2010

(30) Foreign Application Priority Data
Mar. 31, 2003 (AU) .................................. 2003901871

(51) Int. Cl.
*G01N 1/30* (2006.01)
*G01N 1/31* (2006.01)
(Continued)

(52) U.S. Cl.
CPC ................. *B01L 3/545* (2013.01); *B01L 9/523* (2013.01); *G01N 35/00029* (2013.01); *G02B 21/34* (2013.01); *G01N 2035/00079* (2013.01); *G01N 2035/00138* (2013.01);
(Continued)

(58) Field of Classification Search
USPC ............................................................ 436/46
See application file for complete search history.

(56) References Cited

U.S. PATENT DOCUMENTS 4,678,752 A 7/1987 Thorne et al.
4,731,335 A 3/1988 Brigati
(Continued)

FOREIGN PATENT DOCUMENTS

CN 1153305 A 7/1997
EP 0 485 816 A2 5/1992
(Continued)

*Primary Examiner* — Yelena G Gakh
*Assistant Examiner* — Michelle Adams
(74) *Attorney, Agent, or Firm* — Sughrue Mion, PLLC (57) ABSTRACT

A mixing vial is provided for an automated biological reaction apparatus typically used for staining tissue samples in Immuno-histological and in-situ hybridisation reactions. The mixing vial allows reagents placed on the apparatus to be mixed together to form additional or blended reagents. A reagent dispenser mounted on a robotic arm withdraws reagent from the reagent containers and deposits it into one of the mixing vials. Several reagents can be deposited into each vial. Mixing is undertaken by withdrawing the reagents in a vial and re-dispensing the reagent back into the vial. Mixing may take place between the operation of other tasks performed by the apparatus, and a scheduler is used to ensure blended reagent is provided before it is required in one of the processes undertaken on the apparatus. The apparatus is able to automatically identify which blended reagents are required and when they must be applied to provide an appropriate schedule that minimises time taken to stain samples.

28 Claims, 6 Drawing Sheets

(51) Int. Cl.
*B01L 3/00* (2006.01)
*B01L 9/00* (2006.01)
*G01N 35/00* (2006.01)
*G02B 21/34* (2006.01)
*G01N 35/10* (2006.01)

(52) U.S. Cl.
CPC ............ *G01N 2035/00752* (2013.01); *G01N 2035/1025* (2013.01); *Y10T 436/112499* (2015.01)

(56) References Cited

U.S. PATENT DOCUMENTS

| | | | |
|---|---|---|---|
| 4,790,640 A | 12/1988 | Nason | |
| 4,985,206 A | 1/1991 | Bowman et al. | |
| 5,023,187 A | 6/1991 | Koebler et al. | |
| 5,167,922 A * | 12/1992 | Long | 422/404 |
| 5,225,325 A | 7/1993 | Miller et al. | |
| 5,573,727 A | 11/1996 | Keefe | |
| 5,595,707 A | 1/1997 | Copeland et al. | |
| 5,609,822 A | 3/1997 | Carey et al. | |
| 5,719,059 A | 2/1998 | Mimura et al. | |
| 5,800,056 A * | 9/1998 | Suzuki et al. | 366/152.4 |
| 5,804,141 A | 9/1998 | Chianese | |
| 5,985,669 A | 11/1999 | Palander | |
| 6,070,476 A | 6/2000 | Shine et al. | |
| 6,180,061 B1 | 1/2001 | Bogen et al. | |
| 6,337,490 B1 | 1/2002 | Furusato et al. | |
| 6,349,264 B1 | 2/2002 | Rhett et al. | |
| 6,673,620 B1 | 1/2004 | Loeffler et al. | |
| 6,810,921 B2 | 11/2004 | Schlösser | |
| 7,400,983 B2 * | 7/2008 | Feingold et al. | 702/31 |
| 2002/0072122 A1 | 6/2002 | Copeland et al. | |
| 2002/0090730 A1 | 7/2002 | Eckert et al. | |
| 2002/0098116 A1 * | 7/2002 | Sugaya et al. | 422/64 |
| 2002/0155616 A1 * | 10/2002 | Hiramatsu | B01L 3/545 436/165 |
| 2003/0077329 A1 | 4/2003 | Kipp et al. | |
| 2004/0033610 A1 * | 2/2004 | Lovell | B01L 3/5085 436/43 |
| 2004/0053302 A1 | 3/2004 | Livak et al. | |
| 2004/0120855 A1 | 6/2004 | Reichel et al. | |

FOREIGN PATENT DOCUMENTS

| | | |
|---|---|---|
| EP | 1 118 379 A2 | 7/2001 |
| EP | 1 174 702 A1 | 1/2002 |
| JP | 62-98231 A | 5/1987 |
| JP | 62-119460 A | 5/1987 |
| JP | 5-504627 A | 7/1993 |
| JP | 8-129014 A | 5/1996 |
| JP | 10-512048 A | 11/1998 |
| JP | 2001-41954 A | 2/2001 |
| JP | 2002-181676 A | 6/2002 |
| JP | 2003-507715 A | 2/2003 |
| JP | 2003-83992 A | 3/2003 |
| JP | 2003-88367 A | 3/2003 |
| JP | 2003-536058 A | 12/2003 |
| JP | 2004-522979 A | 7/2004 |
| WO | 01/04634 A1 | 1/2001 |
| WO | 01/13128 A1 | 2/2001 |
| WO | 01/40760 A1 | 6/2001 |
| WO | WO 01/51909 A1 | 7/2001 |
| WO | 01/94635 A2 | 12/2001 |
| WO | 03/012454 A1 | 2/2003 |
| WO | 2004/001390 A1 | 12/2003 |

* cited by examiner

METHOD AND APPARATUS FOR FLUID DISPENSATION, PREPARATION AND DILUTION

FIELD OF THE INVENTION

An apparatus and method will be described for dispensing and preparing fluids. In one form the apparatus and method relate to preparing fluids for dispensing onto samples by an automated biological reaction apparatus.

BACKGROUND OF THE INVENTION

Some fluids used in reactions have a short shelf life. Fluid that is not used within a specified time frame can therefore be wasted. Further, the properties of some fluids change over time and it is useful to have fresh reagent available when required. Typically fresh fluid, such as a reagent to be applied during a chemical reaction or test, has been prepared manually as required for application to samples.

Fluids such as reagents may be applied to tissue samples by an automated biological reaction apparatus. Such an apparatus is used to apply reagent to a plurality of slides. Each slide may require a different test, and therefore require a different reagent to be applied to the sample contained thereon.

In instruments as described above, it can be desirable to schedule the dispensation of fluid onto the slides, to minimise the processing time. Scheduling of the tests for each slide can be difficult.

SUMMARY OF THE INVENTION

In one form the present invention relates to a method of preparing a blended reagent in an automated staining apparatus including:
  ascertaining whether a blended reagent is required,
  preparing the blended reagent before its application is required.

Preferably the reagent is moved by a dispenser attached to a robotic arm from the reagent containers to the mixing vial.

In one form the dispenser mixes the reagent together.

Preferably the mixing is accomplished by dispensing the components of the reagent into the mixing vial, withdrawing fluid from the mixing vial, and re-dispensing the fluid into the mixing vial to promote mixing of the components of the reagent.

In another form the present invention relates to a method of scheduling application of reagent to a number of slides in an automated biological reaction apparatus including:
  grouping at least one group of slides together as a batch;
  ascertaining whether a blended reagent is to be applied to any slide within the batch;
  scheduling the step of preparing the blended reagent before the step of applying the blended reagent to the slide.

Preferably the scheduling involves dividing the batch into steps to be undertaken; ascertaining which step requires the application of blended reagent, and inserting the step of producing the blended reagent before the application of the blended reagent is required.

In one form the step of extracting the reagent to make the blended reagent is classified as a batch and scheduled in with the other batches.

In one form the time of preparation of the recording time of blended reagent preparation and comparing expiration time to scheduled application time to ensure blended reagent is fresh.

In another form, there is provided a method of mixing reagent including placing individual component parts of a reagent into a mixing vial using a dispenser, and withdrawing a portion of the resulting reagent into the dispenser, then re-dispensing the reagent, to additionally mix the reagent.

In another form there is a provided an automated biological reaction apparatus having a mixing vessel, reagent containers holding components of a blended reagent, a robotic arm adapted to move a dispenser from the reagent containers to the mixing vessel and a controlling computer, whereby a blended reagent is created by dispensing reagent into the mixing vial.

In one form the mixing vial includes a mount, a plurality of mixing chambers, and an identification means.

BRIEF DESCRIPTION OF THE DRAWINGS

Specific examples of methods and apparatus for fluid dispensation and preparation will be discussed, with reference to the following figures.

Figure 1:
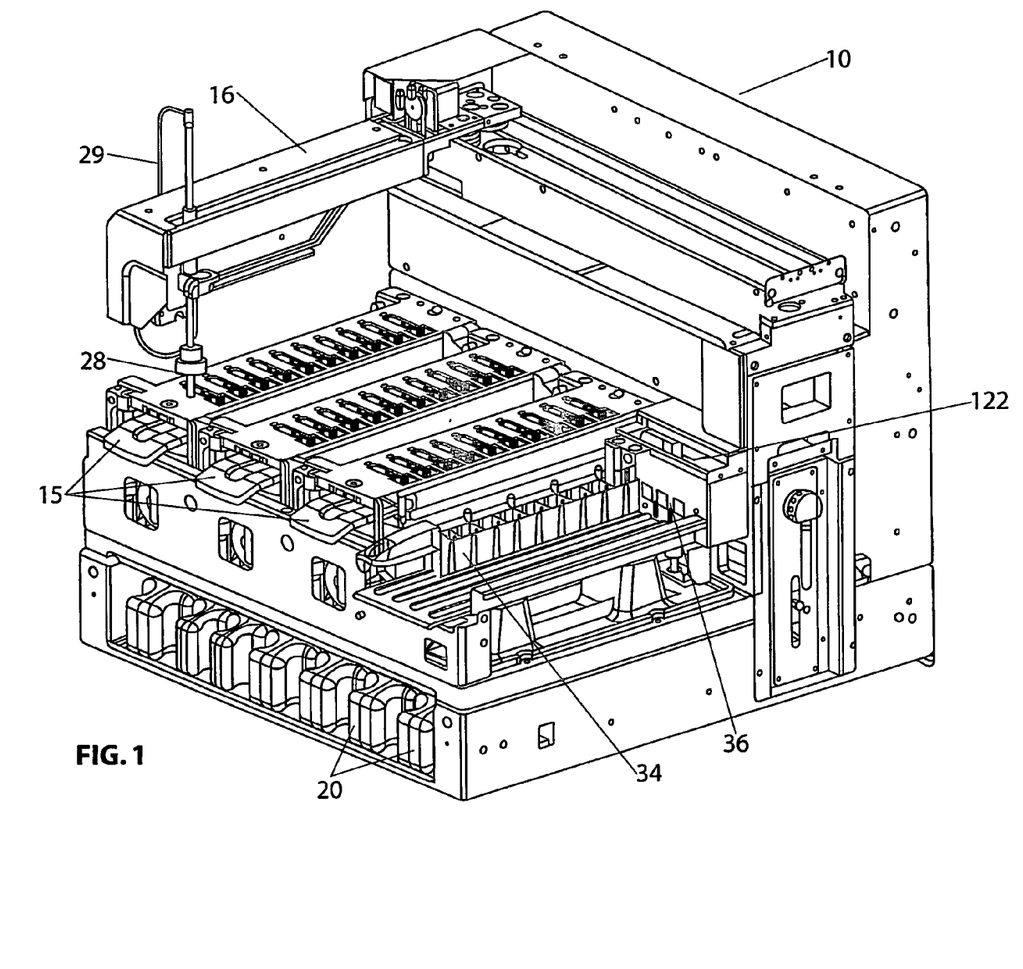
FIG. 1 shows a first isometric view of an Automated Biological Staining Apparatus having a mixing station.

An example of an apparatus used to apply fluids, such as reagent, to samples, is shown in FIG. 1. The automated biological reaction apparatus includes a remote computer (not shown) and a processing module 10. The automated biological reaction apparatus of the present example is described in Australian Provisional Patent Application No. PS 3114 entitled "A Method and Apparatus for providing a Reaction Chamber", from which WO/2004/001390 entitled "Biological Reaction Apparatus with Draining Mechanism claims priority. The contents of the aforementioned document are hereby incorporated by reference.

Figure 2:
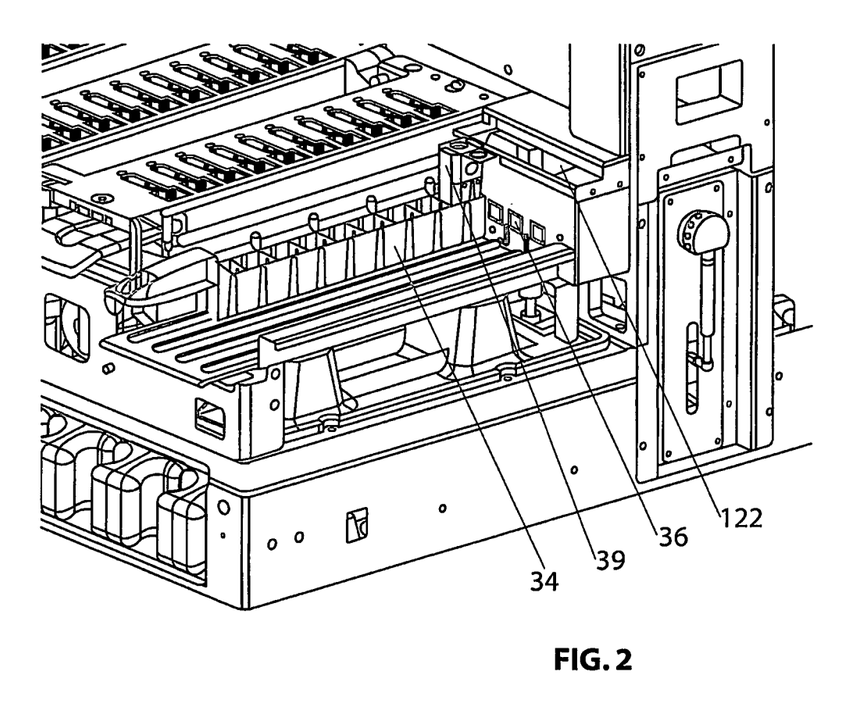
FIG. 2 shows a second isometric view of the mixing station of FIG. 1.

The processing module 10 includes a robot arm 16 having a pipette 28 connected to pumps by tubing 29. The apparatus has a number of bulk reagent containers 20, slide trays 15, and a reagent rack receptacle 36 for receiving reagent racks. A single reagent rack 34, as shown in FIG. 2, may support a number of reagent containers 39.

Figure 4:
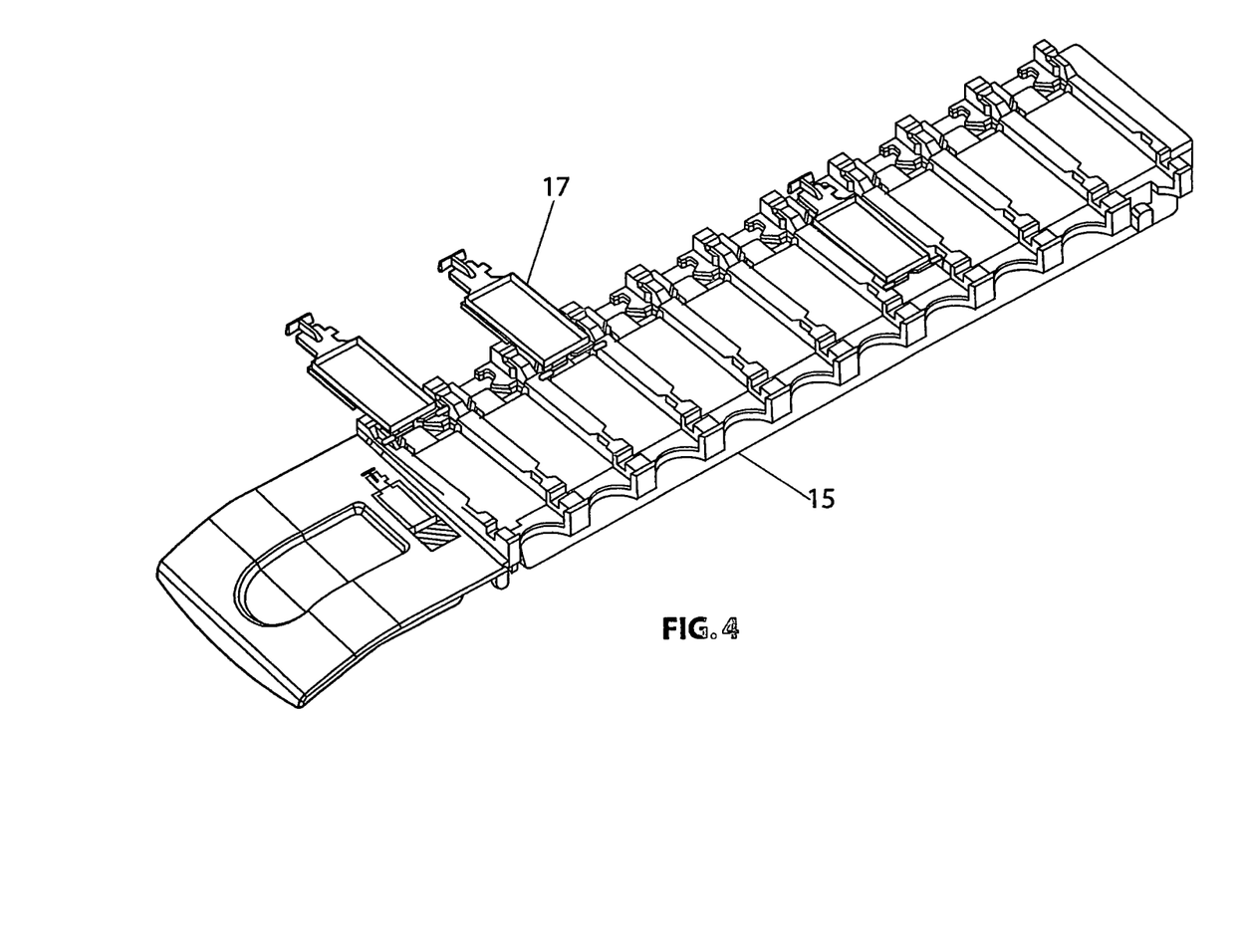
FIG. 4 shows an isometric view of slide rack used with the Automated Biological Reaction Apparatus.

In the present example, the processing module 10 may be loaded with one or more slide trays 15 as shown in FIG. 4. Each slide tray 15 will have at least one slide (not shown), and each slide typically contains a tissue sample (not shown). The slides and tissue samples are, for example, microscope slides having a thin tissue sample mounted thereon, commonly used for histological testing. The slide may also contain a slide identifier, such as a bar code, which uniquely identifies the slide and the sample contained thereon. In the present embodiment, the samples on the slides are covered by a covertile 17 which protects the sample from dehydration and provides a reaction chamber for reagents, which are applied by the pipette 28 of the processing module 10.

Figure 9:
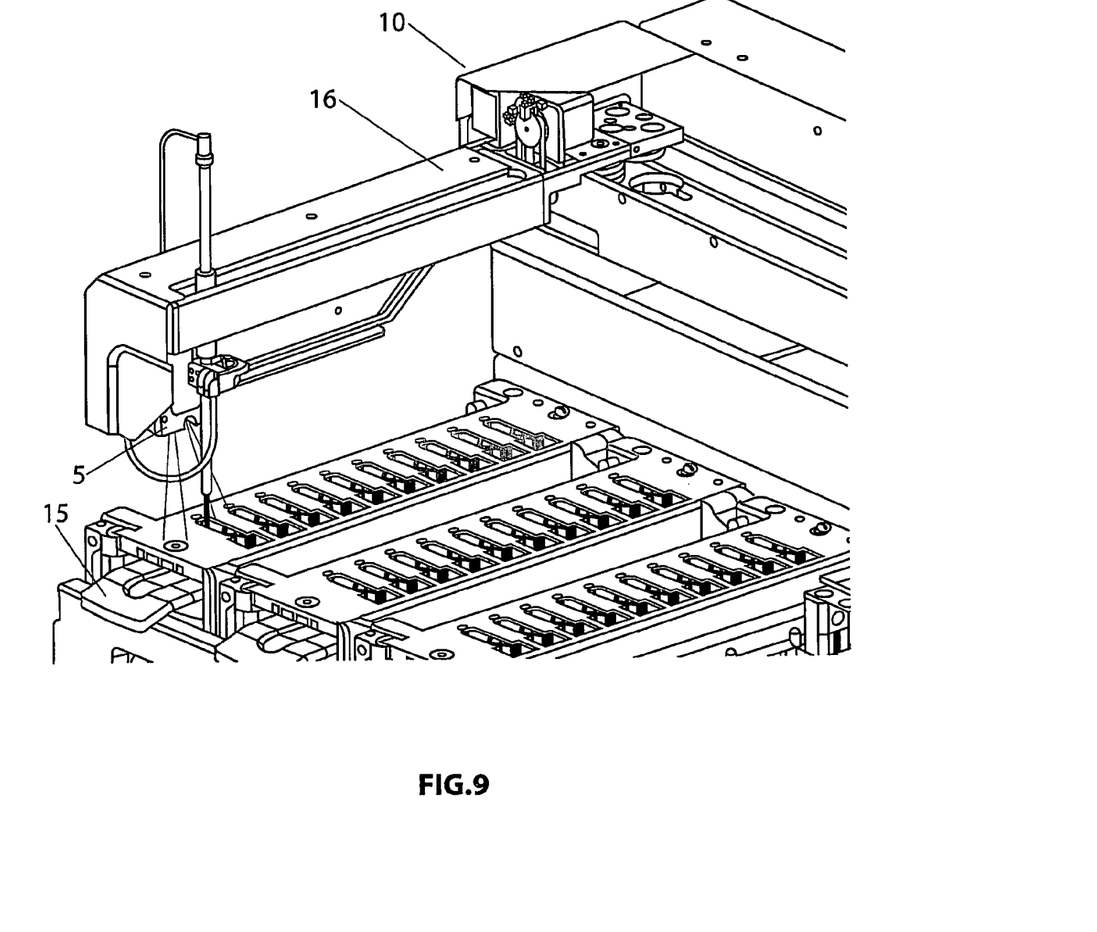
FIG. 9 shows a partial isometric view of a dispenser mounted to a robot arm on the Automated Biological Reaction Apparatus of FIG. 1.

When a slide tray 15 is loaded, the robotic arm 16 moves to be adjacent the slide tray 15, and an electronic scanner such as a bar code reader 5 mounted to the robotic arm 16 reads the bar code on each slide, as shown in FIG. 9. The information relating to the slide is then stored in a memory of a controller (not shown) for the processing module 10, and the remote computer is sent the slide identifier information. The remote computer contains a database holding protocol information in relation to each slide. Protocol information includes all the information to run the histological test, for example Immunohistological tests, In-situ hybridisation test, Fluorescent insitu hybridisation, and other such tests. The present invention is not limited to a specific type of test, but may be useful for types of tests applied to samples where there are a number of steps involving application of reagent and incubation periods following application of said reagent. In an alternative embodiment the database holding the information may be contained within the processing module 10.

There are usually a limited number of reagent containers 39 that may be accessed by the processing module 10. In the processing module 10 of the present example has are four reagent trays 34, each holding a maximum of nine reagent containers 39, for a maximum of thirty six reagent containers 39. Each reagent container may be independent of the other reagent containers, and each reagent container includes a unique identifier (not shown) such as a bar code or optically readable characters. When a reagent rack 34 containing a number of reagent containers 39 is loaded onto the processing module 10, the robotic arm 16 moves along the reagent rack 34 to scan the identifiers on each reagent container 39 with the bar code reader 5. Information relating to reagent content and position of individual reagent containers is stored in the controller of the processing module 10.

Other reagent containers, such as bulk reagent containers 20, are included in the body 12 of the processing module 10, adding to the type of reagents that may be dispensed onto the slide. Some bulk reagent containers 20 contain fluids required for washing and hydrating samples.

In one form, the reagent rack 34 may be used to contain a detection kit. A detection kit consists of a number of reagents in separate reagent containers 39 that are used to perform a particular test on one or more samples. Such a detection kit may include, for example, nine reagent containers 39 to perform a single test, and in the present example this reduces the number of reagent containers 39 available to other slides to twenty seven.

Typical reagents applied to samples on slides include primary antibodies, such as those sold by Novocastra Laboratories Ltd. These reagents are normally supplied in the reagent containers 39 in volumes typically between 7 ml and 30 ml. Other reagents and fluids, such as buffers and de-ionised water, may be kept in the bulk storage containers 20 which typically have volumes between 1-4 liters.

Some reagents, once prepared for application to a sample, have a relatively short shelf life. Therefore, either the reagent is supplied pre-mixed in a ready-to-use formulation, whereupon it must be used within a short period of time from ordering, or it may be prepared by laboratory staff prior to use, and placed into an appropriate reagent container. Some of the reagents, such as 3',3-diaminobenzidine(DAB), when in a final form, begin to degrade soon after preparing and may not be useable more than 24 hours after initial preparation. This requires a new batch to be prepared every day, and ensuring that old batches are discarded after use. Further, enzymes such as protease may need to be applied in varying concentrations depending on factors such as tissue type, other reagents to be applied etc. This can result in numerous batches of reagents being required to be prepared before application to the samples, with the associated problems such as correct application, expiry date, correct mixing, tracking and traceability.

Concentrated primary antibodies may also require preparation before use, requiring dilution before application to a sample. Primary antibodies can be supplied either in a concentrated form or pre-diluted ready-to-use. However, it may be necessary to have several different working dilutions of the same antibody on a single processing module 10, which would otherwise take up several locations in the reagent rack 34. It may therefore be advantageous to have a single reagent container 39 of an antibody, where diluting of the antibody reagent may take place before the reagent is applied to the sample. The primary antibody may be diluted by a primary antibody diluent such as ABDIL 9352 sold by Vision BioSystems Ltd.

Figure 3:
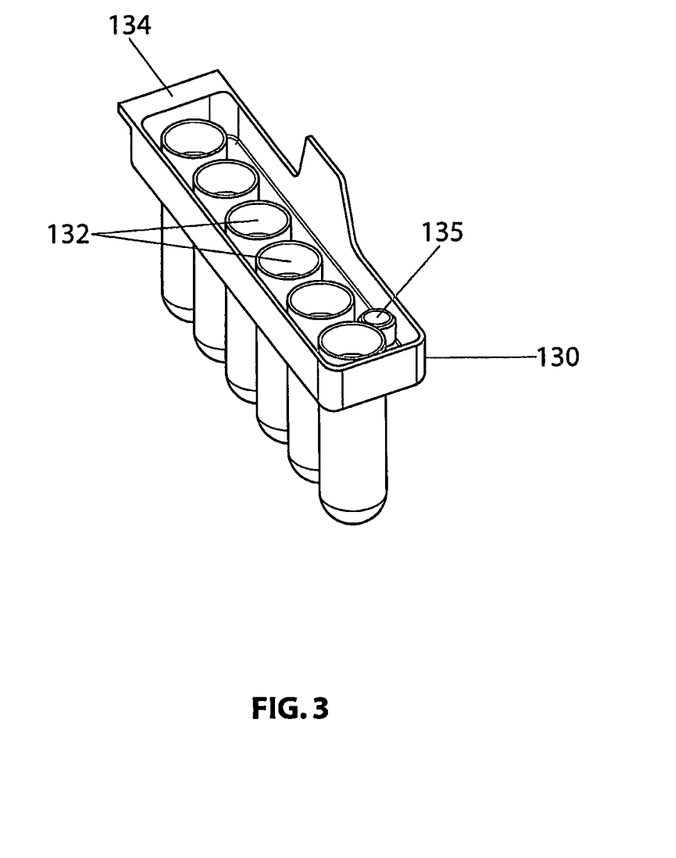
FIG. 3 shows an isometric view of an insert for the mixing station of FIG. 2.

In the present embodiment of the processing module 10, a mixing station 122 is provided, as shown in FIG. 2. Mixing station 122 includes provision for an insert 130 having a number of mixing vials 132, as shown in FIG. 3. The insert 130 in this example has six vials, each vial able to hold a different reagent, although the number of vials can vary. The vials 132 are shown all the same volume, but may vary in volume according to requirements. Typical volumes may be 7 ml per vial.

Also mounted to the insert 130 is a tab 134. Tab 134 may be used to identify the insert 130 such as by way of an identifier such as a barcode. It is envisaged that as the insert 130 is disposable, but may be re-used a number if times before being replaced. Each vial in the insert may contain a different reagent, and may be washed during or between runs. The bar code on the insert 130 may be used to identify the insert 130 so that the controller knows when to discard the insert 130, and request that a new insert be loaded into the mixing station 122. This may be predetermined after a set period of time or uses.

Also shown on insert 130 is an overflow aperture 135, which is adapted to allow excess fluid to drain from the insert should any of the vials 132 overflow.

In operation, after loading and scanning of the slides, the information from the slide bar codes may be cross-checked with the database in the remote computer to establish which series of reagents is to be applied to each slide. The processing module 10 then compares the reagents required, to the reagents currently loaded. If a reagent is identified as being required, and it is of a type that requires preparation, then a preparing step is scheduled into the order of tasks to be undertaken on the processing module 10. The processing module 10 identifies reagents required for tests and classifies reagents as either final form reagents (those that are not to be blended) or those which may be blended. The processing module 10 can request a reagent to be loaded into a reagent tray if it is required, including a reagent that is a part of a blended reagent, if not all parts are available. In this way the processing module can ensure that all necessary reagents are on-board before beginning a staining run.

In one example, three reagent containers (identical to reagent container 39 located in the reagent rack 34), each having a component part A, B, and C of a blended reagent such as DAB, may be located on the processing module 10. In the present example DAB will be mixed in a ratio of 1 part A to 25 part B to 1 part C. To mix a batch of DAB ready for use, the robotic arm 16 first moves to the reagent container containing part A, and withdraws a set volume of part A of the reagent. The robotic arm 16 then moves to one of the vials 132 at the mixing station 122 and deposits the volume into one of the vials 132. The pipette 28 then moves to a washing station located next to the mixing station 122, where the outside and inside of the pipette 28 are rinsed. Once cleaned, the robotic arm 16 moves the pipette 28 to the reagent container containing part B of the reagent. The pipette 28 withdraws the reagent (25 times the volume of part A) and moves to the vial containing part A. Once deposited in the vial, the pipette 28 moves to the washing station and is again washed, before moving to the reagent container holding part C of the reagent. The same volume as removed from the container holding part A is removed, and the pipette 28 moves to the original vial and deposits the reagent with the other reagents. Initially depositing the reagents into the mixing vials causes some mixing, however additional mixing can be accomplished by withdrawing some or all of the reagent from the vial 132 into the pipette 28, then re-depositing the reagent into the vial 132. The pipette may move vertically to ensure that the tip is above the fluid level when depositing to aid the mixing process. The energy of re-deposition causes the reagents to mix more readily. This mixing process can be undertaken a number of times as desired. After the reagent has been mixed sufficiently, the pipette 28 may proceed to the wash station if the next reagent to be applied to a sample is not DAB. This volume of the vials and the amount withdrawn by the pipette provide a sufficient volume of DAB for many applications to samples. Whenever DAB is required, the robotic arm moves the pipette 28 to the vial where the DAB was mixed, as the position of the vial in which mixing of particular reagents is recorded by the controller. The time of the preparation is also recorded, so that after a predetermined period of time the mixed reagent can be discarded. This prevents the prepared reagent from being used after expiring. A number of vials may contain mixed reagent at once, as the position of each vial and its contents is recorded.

After completion of testing for the day, or at the expiry of the DAB, the vial 132 containing the DAB (or any other reagent that has expired) can be cleaned as discussed below.

The example described above may be an automated process whereby once the protocols of the samples are entered and correlated with slide identifiers, the processing module can determine which reagents are required to complete the tests runs.

While the above process is automated, the resources employed (robotic arm 16 and pipette 28) may be utilised for significant periods of time in general reagent application to samples, and are therefore a critical resource on the processing module. The robotic arm 16 cannot perform two tasks at once, and therefore when scheduling one task, another task may need to be delayed. Delays can cause problems as, for example, a delay in applying a hydrating fluid may cause tissue samples to dry out, or a delay in applying wash fluid may cause tissue samples to be exposed to reagent longer than desirable. It is important that variability of test results be avoided in the various types of tests mentioned herein. For this reason the processing module 10 can be programmed to prepare reagents in the absence of any samples, and the volume and concentrations are user determinable through a user interface (not shown). However, it is also possible to schedule the blending of reagents required in a test run during the processing of the samples, as there are times when the critical resources of the processing module (e.g. the robotic arm 16) are not in use. This produces several benefits including:

reducing the time to run a test (by removing the necessity to prepare the blended reagent beforehand);

providing certainty of type and volume of blended reagents required (due to the automated nature of determining protocols to be applied to each slide);

reducing wastage of blended reagents;

ensuring blended reagent used is fresh (blending takes part during, not before the run, and the instrument can verify precisely when the blended reagent was made);

tracking blended reagent, as the processing module scans each component of the blended reagents (except bulk reagent) and therefore knows which batch each component came from should there be quality issues; and reducing variability by having the processing module 10 do the same task time after time, it reduces human variability within a laboratory.

Other benefits include the mixing of blended reagent by the pipette 28, ensuring that the prepared reagent is fully mixed before application to a sample, and providing a better uniformity of mixing than, for example, applying components of the reagent directly to the sample and mixing on the sample.

Other examples of reagents that benefit from mixing on the processing module 10 include protease, which may be required to be applied in a number of concentrations. In the above example, only one reagent container of protease would be required in the reagent tray 34, and several concentrations of protease may be prepared by the processing module 10 using diluent stored on board either in a reagent container 39 or bulk reagent container 20. These different concentrations may be placed in different vials 132 for later use.

Scheduling

In relation to scheduling of mixing within a batch, specific details of scheduling are disclosed in Australian Provisional Patent Application No. 2003900810 entitled "Method of Scheduling" filed 24 Feb. 2003 by same applicant, from which WO/2004074847 claims priority), the contents of which are hereby incorporated by reference.

The types of protocols are predefined by the system, so during registration it is merely a matter of selecting one from a list. It is possible to create your own protocol and save it to the list for later use.

In one example of operation of the processing module 10, to get the instrument to process the slides, a slide tray having at least one registered slide is loaded into the processing module 10. At this point the robot arm 16 having the bar code reader 5 will read the bar codes of all the slides in the trays 15 and look up their respective bar code IDs. The bar code ID will correspond to a slide ID, and the slide ID will be associated with primary antibody and protocol information, which includes a list of all the reagents to be applied, and length of time of exposure of the sample to the reagents. The times in the protocol may have some ranges, e.g. 5-8 minutes.

This process is done for every different slide in a slide tray (say, slide tray 1). After reviewing all the slides and ascertaining the primary antibodies required and protocol information, the instrument checks to see if it has correct type and sufficient quantity of reagents on board. This being the case a protocol is constructed for the all slides. This is not complicated, as in the present example all slides within a tray must have the same (or compatible) protocol. This means that while different primary antibodies may be applied to each sample on a slide, the timing within different protocols will be generally the same. Information within the protocol includes the sequence of steps, and information on each step including:

Durations of each step

Potential open times for a step

Each step duration has two times, being a use time and an open time:

Use time is time when a shared resource is in use. Typically this means the robotic arm, but can mean other hardware of the Bond instrument.

Free time is time where the duration of a step has not completed, but the shared resource is not in use. Typically this is during incubation of the sample after reagent has been applied.

As an example, if a slide is to have a primary antibody applied to the sample, then the time taken to undertake that step includes moving the robot arm to the correct reagent container, withdrawing the right amount of reagent using the pipette, moving to the slide, dispensing the antibody, and moving to a wash station to wash the pipette. However, the primary antibody must be in contact with the sample for a predetermined period of time before being washed off. Therefore, the step is not finished until the primary antibody is washed off, however the robot arm is not required during the incubation, until the washing step.

Also, a step is not just for a single slide, but for as many slides as are present in the tray when it is loaded. Thus if the tray has 10 slides, then all the slides will be processed in a single step. An example would be during dispensation of a primary antibody on each slide. While the protocols must all be compatible, the primary antibodies may be all different. However, the instrument in this example is designed so that different primary antibodies all have the same incubation time, and therefore, apart from being sourced from different reagent containers, and the requirement for pipette washing when changing primary antibodies, the robotic arm moves from reagent container to slide, to dispense primary antibody onto each slide in the tray, before waiting for the incubation period to end.

A step may also not necessarily be related to a slide at all. For example, after the run begins, one of the early steps may be the mixing of the DAB, as described above. This step must be inserted into the sequence of operations of the processing module so that the blended reagent is ready before it is due to be applied.

As mentioned above, it may be detrimental to the tests if one step (for example washing off primary antibody from slides) is delayed due to the insertion of another step (for example preparing blended reagents). In the protocol, this maximum allowable time is referred to as an Open time:

Open Time: the maximum legal time that the next "block" may be delayed.

Thus a the system will generate a protocol for slide tray 1 comprising a number of blocks, each block having a number of steps, each step having at least a use time. Blocks are separated by open times. An open time is stored as a maximum time, in that it could be any time between its maximum time and zero. The amount of actual open time used in a protocol is not known until after the schedule has been finalised.

Figure 5:
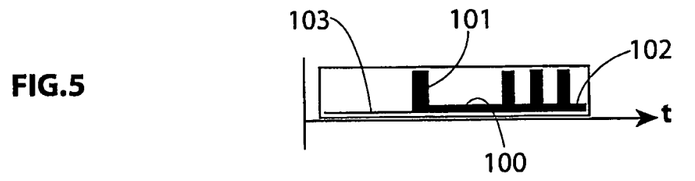
FIGS. 5-8 show graphical representations of batches being scheduled on the Automated Biological Reaction Apparatus of FIG. 1.

In FIG. 5, the tall rectangles 101 represent use times (for example robotic arm in use time), the short ones 102 represent free times (no critical resources in use, such as during an incubation period) and the elongate one 103 represents the maximum allowable open time. The horizontal axis 104 is time, and so the width of a rectangle 101,102,103 represents its duration.

Figure 6:
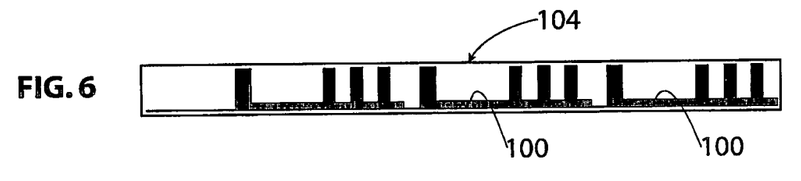

A protocol 104 for the batch consists of one or more of these blocks 100, as illustrated in FIG. 6.

A schedule is built for each slide tray placed into the Bond instrument. Each slide tray may have up to 10 slides. Each slide tray may use a different protocol, however the protocol should be compatible or the same for each slide within a tray.

After all the trays are entered and the protocols for each tray or batch have been worked out, as above, the scheduler will attempt to interleave the individual schedules for each tray to make an single schedule that minimises the overall run time of the system. Typically this can happen when two or more trays start at the same time, or when a single tray has started, and one or more other trays are loaded into the instrument. However it may occur when the processing module has a tray loaded, and upon scanning the slide identifiers, it ascertains that a blended reagent is required, and that none already exists on-board.

The instrument will have divided each protocol into a number of blocks. Blocks contain at least one step. Each step has at least a use time, and often an open time. As mentioned above, blocks are separated by open times. If there is no open time between steps, then it follows that the second step must commence immediately after the previous step, and therefore these two steps are bound together by the scheduler in a block, as it would be impossible to schedule anything between the two blocks without violating the rule of the open time being zero.

Therefore, after reading a tray of slides and determining the a blended reagent is required, the instrument will have two batches stored as schedules, each batch divided into a number of blocks, each block separated by open times. The scheduling program then looks at a first batch and determines the use and free times of each step within the batch. There are several facts to consider: use time violations and open time violations.

Use time violations are where the critical resource is required to be in use by two batches at the same time. This cannot physically occur, as for example, the robot arm cannot be in two places at once and therefore cannot dispense fluid onto two different slides at the same time. The scheduler therefore has to make sure that if blocks overlap, the use times within a block do not overlap.

Figure 7:
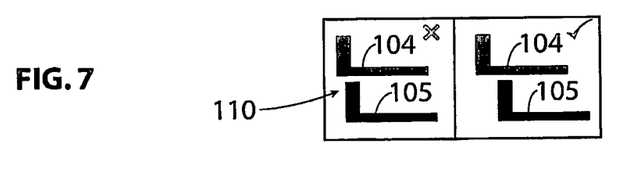

In FIG. 7, the schedule 110 on the left shows batches 104,105 which are both trying to use the common resource at the same time. This is a use-time violation. The use times on the right hand side do not overlap, and therefore there is no violation.

In order to avoid use time violations, blocks 100 in a schedule can be delayed. However, blocks cannot be delayed indefinitely. When a block is delayed by a time that exceeds the predetermined open time, this is called an open time violation. For example a slide may require application of fluid within a predetermine time (e.g. 10 minutes) to prevent drying of the sample on the slide. If the schedule does not allow for application of fluid within the predetermined period then this is an open time violation. This can result in inconsistent staining or tissue drying out.

In FIG. 5, the line or rectangle 103 on the left-hand side represents the open time for the block 100, which is the maximum amount of time that the block can be delayed after the end of the previous block from the same batch 104. This line 103 must overlap with the previous block, or extend to before a start time of the schedule, in order for the block's open time to not be violated.

Figure 8:
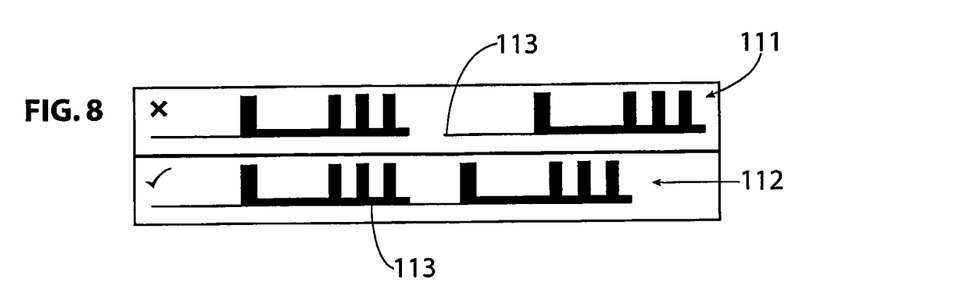

In FIG. 8, the top section 111 shows a block 100 whose open time is being violated. The bottom section 112 shows a start time 113 of this block 100 adjusted so that its open time is not violated.

Worst case scenario for scheduling would be a second batch not starting until the first batch had completed the processing. The best case is where the finishing point of the second batch is not delayed by the first batch. Typically a solution exists between these points and a number of calculations are run to find one or more solutions. Computing power limits the number of tries a computer has to get a solution, and typically more than one solution will be sought from a scheduling run. If more than one successful schedule is achieved, then the schedules are compared and the best schedule selected.

In the present example, the blended reagents are prepared in a mixing batch by using the robotic arm to move to a first reagent container and withdraw a sample of the reagent, and move to the mixing vials to deposit the sample. It will usually be necessary to wash the dispenser before and after this step. The wash steps and the dispense step form a use time of a block of the batch for blending reagents. There is no free time in this case as no incubation or reaction periods are generally necessary, however if a reaction time is necessary, this become free time as the robotic arm will not need to be in use. The open times between blocks can be very large as the reagents are generally stable within by themselves. Thus the first three blocks of the mixing batch (for DAB) are associated with drawal and dispensation of the three fluids and associated washing steps. A fourth block is the mixing of the reagents by withdrawing some or all fluid from the mixing vial, and re-dispensing it to aid the mixing of the reagents. These four blocks can be interleaved with blocks of other batches to provide blended reagent on board the processing module. Ideally the blocks of the mixing batch are slotted into free times of the staining batches (batches associated with the samples on the slide trays). However, if there are no appropriate free times in the staining batches, then open times, which are ideally of zero time duration but may be extended up to their predefined maximum times, may be used. The above holds true if there are one or several staining batches.

In order to ensure that the mixing batches are completed before the blended reagent is required, a constraint in the scheduling is employed. The final block of the mixing batch is a slave batch to any other block in a staining batch that requires the blended reagent. Being a slave block, it must be complete before scheduling of the master block. Using this constraint the mixing batch is completed before the blended reagent created by the mixing batch is required.

Cleaning

After blended reagent is prepared, and it is applied to samples, remaining or expired blended reagent is siphoned to waste by the aspirator. The vials 132 may then be cleaned. Cleaning is undertaken by draining any prepared reagent remaining after the required prepared reagent has been dispensed. Draining is done with the pipette 28, the drained fluid being directed to an internally plumbed bulk waste container. Once substantially empty, a rinse cycle is undertaken. The rinse cycle may use a cleaning solution, which for example could contain an alcohol such as Industrial Methylated Spirits (IMS) dispensed into the vial 132. The cleaning solution is then drained via the pipette 28. More than one rinse cycle may be undertaken. After removing cleaning solution for the final rinse, any remaining cleaning solution is allowed to evaporate to completely empty the vial.

It is also possible to revisit the mixing vial after a predetermined time from initial preparation, to re-mix the reagent. This may be done by withdrawing some of the prepared reagent into the pipette 28, and redispensing into the same vial 132. This may be important where components of the prepared reagent settle after time or do not stay mixed after a period of time. As with initial mixing, the remixing step may be scheduled during a period of inactivity of the robot arm and aspirator.

In an alternative embodiment, a reagent container 39 may be used as a mixing vial. In one form the reagent container 39 may be empty, and have an identification means such as a bar code label uniquely identifying the container. In another form the reagent container may contain reagent that requires the addition of other reagent and mixing may take place in a similar way as described above. After mixing, the database containing information relating to the contents of the reagent container may be updated so that the processing module always has an accurate record of the contents of the particular reagent container used. The type of reagent container used may be the same as that supplied by Novocastra laboratories for use on the Bond type instrument, or other types of reagent container as appropriate. Generally all that is required is access for the pipette into the reagent container, and therefore reagent container configuration is not important.

It is also not necessary to have the mixing vials identified by a unique identification means if tracking of the reagent container/mixing vial and its contents are not required. However, use of a unique identification means and a scanner on the processing module provide advantages in relation to automation and assist in providing an audit trail of reagent used.

The invention claimed is:

1. A biological reaction apparatus, comprising:
an area configured to hold a plurality of reagent containers holding reagents comprising at least a first reagent container holding a first reagent and a second reagent container holding a second reagent;
a plurality of mixing vessels comprising a first mixing vessel and a second mixing vessel;
an insert configured to hold the plurality of mixing vessels, the insert having an identifier which identifies the insert;
a slide tray configured to hold a plurality of slides;
a robotic device with a dispenser;
a reader; and
a controller which is programmed to control the dispenser of the robotic device to dispense the first reagent from the first reagent container into the first mixing vessel and the second reagent from the second reagent container into the first mixing vessel, thereby allowing the first reagent and the second reagent to be mixed into mixed reagents in the first mixing vessel,
wherein the controller is further programmed to control the dispenser of the robotic device to dispense the mixed reagents from the first mixing vessel onto at least one slide in the slide tray, and
wherein the controller is further programmed to control the reader to read the identifier on the insert and determine time when to discard the insert based on a set period of time or a number of uses.

2. The biological reaction apparatus of claim 1, further comprising a mixing station at which a mixing vessel from the plurality of mixing vessels is located.

3. The biological reaction apparatus of claim 1, wherein said insert is removable from said apparatus.

4. The biological reaction apparatus of claim 3, further comprising a tab provided on the insert and having the identifier thereon for identifying the insert.

5. The biological reaction apparatus of claim 1, wherein said insert includes an overflow drain for draining excess fluid from the insert.

6. The biological reaction apparatus of claim 1, wherein the area for holding the plurality of the reagent containers comprises a reagent tray.

7. The biological reaction apparatus of claim 6, wherein the reagent tray is removable from the apparatus.

8. The biological reaction apparatus of claim 1, wherein the controller is further configured to control the reader to read a unique identifier on a reagent container from among the plurality of reagent containers.

9. The biological reaction apparatus according to claim 8, wherein the slide tray is configured to hold a first slide and a second slide and wherein the controller is further programmed to control the dispenser of the robotic device to dispense a different reagent mixture to the second slide as opposed to the first slide.

10. The biological reaction apparatus according the claim 1, wherein the insert has a tab having the identifier which identifies the insert.

11. The biological reaction apparatus according to claim 1, wherein the controller is further programmed to record a position of the first mixing vessel and the second mixing vessel.

12. The biological reaction apparatus according to claim 1, wherein the controller is further programmed to schedule a plurality of processes for the slides in the slide tray to be executed together and wherein the controller is programmed to control the dispenser of the robotic device to dispense different reagent mixtures to corresponding slides held by the slide tray.

13. The biological reaction apparatus according to claim 1, further comprising an incubator, wherein the slide tray is configured to hold a first slide and a second slide, and wherein the controller is further programmed to control the incubator such that the incubator is configured to incubate the slide tray, which holds the first slide and the second slide, for a predetermined time based on a protocol retrieved from a database.

14. The biological reaction apparatus according to claim 1, wherein the plurality of mixing vessels are formed integrally with the insert.

15. The biological reaction apparatus according to claim 1, wherein the insert is configured to receive the plurality of mixing vessels.

16. An automated biological reaction apparatus comprising:
a plurality of mixing vessels comprising a first mixing vessel and a second mixing vessel;
an insert configured to hold the plurality of mixing vessels, the insert having an identifier which identifies the insert;
an area configured to hold a plurality of reagent containers comprising at least a first reagent container configured to hold a first reagent and a second reagent container configured to hold a second reagent;
a slide tray configured to hold a plurality of slides;
a robotic arm with a dispenser and a scanner; and
a controlling computer which is programmed to control the scanner of the robotic arm and programmed to control the dispenser of the robotic arm to dispense the first reagent from the first reagent container into the first mixing vessel and to dispense the second reagent from the second reagent container into the first mixing vessel, thereby allowing the first reagent and the second reagent to be mixed into mixed reagents in the first mixing vessel,
wherein the controlling computer is further programmed to control the dispenser of the robotic arm to dispense the mixed reagents from the first mixing vessel onto at least one slide in the slide tray , and
wherein the controller is further programmed to control the scanner of the robotic arm to read the identifier on the insert and determine a time when to discard the insert based on a set period of time or a number of uses.

17. The automated biological reaction apparatus according to claim 13, wherein the plurality of mixing vessels are formed integrally with the insert.

18. The automated biological reaction apparatus according to claim 16, wherein the insert is configured to receive the plurality of mixing vessels.

19. A method of preparing a blended reagent in an automated biological reaction apparatus comprising:
holding, by an insert with an attached identifier which identifies the insert, a plurality of mixing vessels, comprising a first mixing vessel and a second mixing vessel;
holding a plurality of slides by a slide tray;
dispensing, by a dispenser of a robotic device, a first reagent from a first reagent container into the first mixing vessel and a second reagent from a second reagent container into the first mixing vessel;
allowing the first reagent and the second reagent to be mixed into mixed reagents in the first mixing vessel,
dispensing, by the dispenser of the robotic device, the mixed reagents from the first mixing vessel onto at least one slide obtained from the slide tray; and
reading, by a reader, the identifier on the insert; and
determining, by a controller programmed to control the robotic device and the reader, a time when to discard the insert based on the identifier and a set period of time or a number of uses.

20. The method of claim 19, wherein the insert has a tab with the identifier.

21. The method of claim 19, further comprising draining excess fluid from the insert via an overflow drain.

22. The method of claim 19, further comprising recording, by the controller, a position of the first mixing vessel and the second mixing vessel.

23. The method of claim 19, further comprising:
scheduling a plurality of processes for the slides in the slide tray, wherein the processes are executed at same time; and
dispensing, by the dispenser, different reagent mixtures to corresponding slides within the slide tray.

24. The method of claim 19, wherein the insert comprises the plurality of mixing vessels.

25. The method of claim 19, wherein the holding of the plurality of mixing vessels by the insert comprises receiving by the insert the plurality of mixing vessels and holding the received plurality of mixing vessels.

26. A method of preparing a blended reagent in an automated biological reaction apparatus comprising:
dispensing, by a dispenser of a robotic arm, a first reagent from a first reagent container into a first mixing vessel and a second reagent from a second reagent container into the first mixing vessel;
allowing the first reagent and the second reagent to be mixed into mixed reagents in the first mixing vessel;
holding, by an insert with an attached identifier identifying the insert, a plurality of mixing vessels comprising the first mixing vessel;
dispensing, by the dispenser of the robotic arm, the mixed reagents from the first mixing vessel onto at least one slide;
reading, by a scanner of the robotic arm, the identifier on the insert; and
determining, by a controlling computer programmed to control the robotic arm, a time when to discard the insert based on the identifier of the insert and a set period of time or a number of uses.

27. The method of claim 26, wherein the insert comprises the plurality of mixing vessels.

28. The method of claim 26, wherein the holding of the plurality of mixing vessels by the insert comprises receiving by the insert the plurality of mixing vessels and holding the received plurality of mixing vessels.

* * * * *